(12) United States Patent
Koenig et al.

(10) Patent No.: US 6,212,798 B1
(45) Date of Patent: *Apr. 10, 2001

(54) POST OPERATIVE SHOE SYSTEM

(75) Inventors: Richard D. Koenig, Pembroke Pines, FL (US); Donald J. Waldron, Florrisant, MO (US)

(73) Assignee: POS Equipe, L.L.C., Weston, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/199,653

(22) Filed: Nov. 25, 1998

(51) Int. Cl.[7] ..................................... A43B 23/02
(52) U.S. Cl. ................................. 36/110; 36/11.5; 602/27
(58) Field of Search ..................... 36/110, 88, 97, 36/11.5, 50.1; 602/60, 61, 62, 65–66, 27

(56) References Cited

U.S. PATENT DOCUMENTS

| | | | |
|---|---|---|---|
| 4,151,662 | * 5/1979 | Vistins | 36/98 |
| 4,178,703 | * 12/1979 | Pols | 36/110 |
| 4,773,170 | * 9/1988 | Moore et al. | 36/110 |
| 4,899,468 | * 2/1990 | Richbourg et al. | 36/110 |
| 5,152,081 | * 10/1992 | Hallenbeck et al. | 36/28 |
| 5,452,527 | * 9/1995 | Gaylord | 36/110 |
| 5,778,565 | * 7/1998 | Holt et al. | 36/110 |
| 5,827,210 | * 10/1998 | Antar et al. | 36/110 |
| 5,885,236 | * 3/1999 | Varn | 602/27 |
| 5,897,518 | * 4/1999 | Shaw | 602/65 |

FOREIGN PATENT DOCUMENTS

2159038 * 11/1985 (GB) ..................................... 36/101

* cited by examiner

Primary Examiner—Paul T. Sewell
Assistant Examiner—Jila M. Mohandesi
(74) Attorney, Agent, or Firm—Robert M. Schwartz; Gerald R. Hibnick

(57) ABSTRACT

A post operative shoe system facilitating recovery or the foot surgical patient is disclosed. The shoe system includes a first pair of shoes employed immediately following surgery, i.e., up to 6–8 weeks following surgery, and a second pair of shoes employed after this initial convalescent period, for a period up to 3–4 months. The first pair of shoes includes in each shoe a pre-configured rigid shoe sole, a counter assembled to the shoe sole which forms a heel, and a releasably adjustable double closure system between inner and outer vamps attached to the shoe sole and a tongue assembled to one of the vamps for releasable adjustable attachment to the other of said vamps. The second pair of shoes includes in each shoe a pre-configured rigid shoe sole with an inner and outer vamp assembled to each shoe sole which is releasably adjustably attached to one another across the top of and around the heel of a user's foot.

16 Claims, 5 Drawing Sheets

POST OPERATIVE SHOE SYSTEM

BACKGROUND OF THE INVENTION

The present invention relates to a post operative shoe system, and more particularly, to a post operative shoe system facilitating recovery of a foot surgical patient.

Various types of shoes and other footwear have been developed for use following post operative surgery and for other therapeutic purposes. While there are many different types and kinds of such footwear, some examples of prior art designs are shown by the therapeutic weight disbursing shoe sole of U.S. Pat. No. 4,738,262; the adjustable semi-flexible health shoe construction of U.S. Pat. No. 4,188,735; the orthopedic shoe construction of U.S. Pat. No. 4,567,678; the removable ankle brace footwear design of U.S. Pat. No. 4,378,793; the adjustable post surgical shoe construction of U.S. Pat. No. 4,178,925; the shock absorbing surgical shoe of U.S. Pat. No. 4,677,767; another post operative shoe construction as shown by U.S. Pat. No. 4,546,557, and the post operative shoe design of design Pat. No. 262,580.

While all of the above constructions have functioned to provide comfort and support to a post operative surgical patient, there have been a number of inherent disadvantages, considering the time of use and the type of injury for which such shoes may be employed. Concerning the time of use, there are different foot support requirements immediately following surgery, for a period of 6–8 weeks, than in a subsequent convalescent period, for example, 3–4 months following surgery. Some therapeutic and post operative shoes may be limited to certain types of foot injuries or problems, and thus will assist in the healing process for a variety of different kinds of foot injuries/problems.

As will be apparent from the discussion that follows, the present invention is a post operative shoe system which overcomes the aforenoted deficiencies of the prior art, while at the same providing improved comfort, stability, convenience, and use by the foot surgical patient in the post operative recovery period.

SUMMARY OF THE INVENTION

Among the several objects and advantages of the present invention include:

The provision of a new and improved post operative shoe system facilitating recovery of the foot surgical patient;

The provision of the aforementioned post operative shoe system which includes a first pair of shoes and a second pair of shoes of different design and construction;

The provision of the aforementioned post operative shoe system in which the first and second pair of shoes provide, in different ways, the necessary comfort, stability, support, convenience and ease of use by the post operative foot surgical patient;

The provision of the aforementioned post operative shoe system in which the first pair of shoes incorporates a unique double closure system including releasably adjustable fastener elements to enable each of such shoes to be held securely in place on a user's foot without any slippage or the shoe at the heel and/or the sensation hat such shoe may be coming off during use;

The provision of the aforementioned post operative shoe system in which the second pair of shoes includes releasable adjustable attachment across the top of and around the heel of a user's foot;

The provision of the aforementioned post operative shoe system which incorporates a soft, comfortable and washable inner lining with a breathable, easy to clean outer lining for each of the shoes in the aforementioned system;

The provision of the aforementioned post operative shoe system which can be used for a variety of different foot injuries/problems including any crushing injury to the foot, any bunion problems, any metatarsal injury to the foot, and/or other foot problems; and The provision of the aforementioned post operative shoe system which is constructed in a durable slip last construction facilitating long wearing and use; is attractive in appearance; easily washed/and or cleaned; can be manufactured by well known shoe manufacturing techniques; and is otherwise well adapted for the purposes intended.

Briefly stated, the post operative shoe system of the present invention facilitates recovery of the foot surgical patient and includes a first pair of shoes employed immediately following surgery, with each such shoe including a pre-configured rigid shoe sole, a counter assembled to the shoe is forming a heel; and an inner and outer vamp assembled to the shoe sole and counter on opposite sides of each shoe and including a toe cut-out section at the front end of each shoe, with the inner and outer vamp on opposite sides of each shoe being releasably adjustably attached to one another. The second pair of shoes employed in the post operative shoe system is used after the initial convalescent period, and includes a pre-configured rigid sole, and an inner and outer vamp assembled to the shoe sole on opposite sides of each shoe and including toe and heel cut outs, the inner and outer vamp on opposite sides of each such shoe being releasably adjustably attached to one another across the top of and around the heel of a user's foot The pre-configured rigid shoe sole in each of the first pair of shoes comprises an outsole and a two part insole including a pre-configured rigid shoe sole insole attached to the outsole and a padded upper insole attached to the pre-configured rigid insole. Each of the second pair of shoes has a pre-configured rigid sole comprising a pre-configured rigid outsole and a padded upper insole.

In each of the first pair of shoes, one of the inner and outer vamps is provided with tongue elements, with the tongue elements and the other of said vamps being releasably adjustably attached to one another, and with one of the vamps also having strap means extending therefrom which are also releasably adjustably attached to the other of said vamps, to provide a double closure fastening system.

In the second pair of shoes in the aforementioned post operative shoe system, the inner and outer vamps are releasably adjustably attached to one another across the top of a user's foot and include heel strap elements extending therefrom which are also releasably attached to one another behind the heel of a user's foot.

In both of the first and second pair of shoe constructions in the post operative shoe system, the inner lining is preferably made from terry cloth lining for comfort and ease of washing, while the outer lining is made from a porous synthetic poyamide material to facilitate breathing and cleanliness.

Other features and advantages of the present invention will become more apparent from the description that is to follow.

BRIEF DESCRIPTION OF THE DRAWINGS

Corresponding reference numerals will be used throughout the several figures of the drawings.

DESCRIPTION OF THE PREFERRED EMBODIMENT

The following detailed description illustrates the invention by way of example and not by way of limitation. This description will clearly enable one skilled in the art to make and use the invention, and describe several embodiments, adaptions, variations, alternatives and uses of the invention, including what we presently believe is the best mode of carrying out the invention.

In order to facilitate recovery of a foot surgical patient, the post operative shoe system of the present invention is employed. The post operative shoe system of the present invention includes a first pair of shoes, constructed along the lines of the shoe shown in FIGS. 1–10 of the drawings, and a second pair of shoes, constructed along the lines of the shoe shown in FIGS. 11–14 of the drawings. The first pair of shoes in FIGS. 1–10 of the drawings is employed immediately following surgery, for a period of approximately 6–8 weeks, whereas the second pair of shoes, constructed like the shoe shown in FIGS. 11–14 of the drawings, would be employed after an initial convalescent period, during the first 3–4 months following surgery. Both of the first and second pair of shoes in the post operative shoe system of the present invention provides comfort, convenience, stability and support for the post operative foot surgery patient in the aforementioned time periods.

Figure 1:
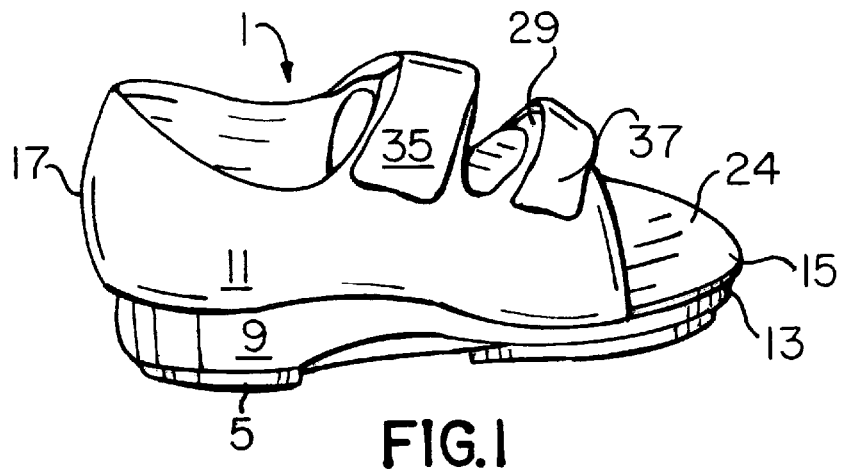
FIG. 1 is a prespective view of a post operative shoe for a foot surgical patient used in the post operative shoe system of the present invention.
Figure 2:
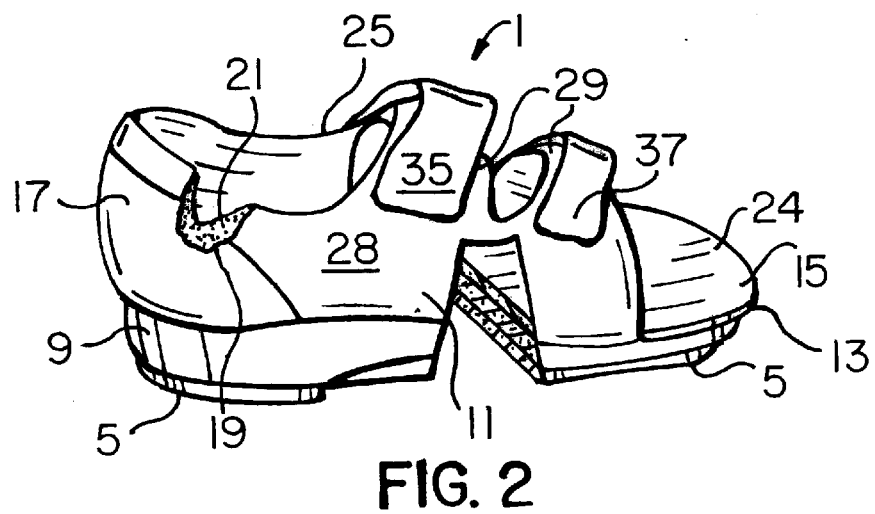
FIG. 2 is a right side elevational view, partially in section, of the shoe illustrated in FIG. 1.

More specifically, the shoe 1 illustrated in FIGS. 1–8 of the drawings, utilizing both left and right foot models, is the first pair of shoe in the post operative system of the present invention. Each shoe utilizes a pre-configured rigid sole which includes, as best seen in FIG. 2, a rubber outsole 5 at the forepart and rearpart of the shoe 1, a rigid sole having a padded upper insole 13 covered by an innerlining 15 and being attached to the pre-configured rigid shoe sole 9.

Figure 4:
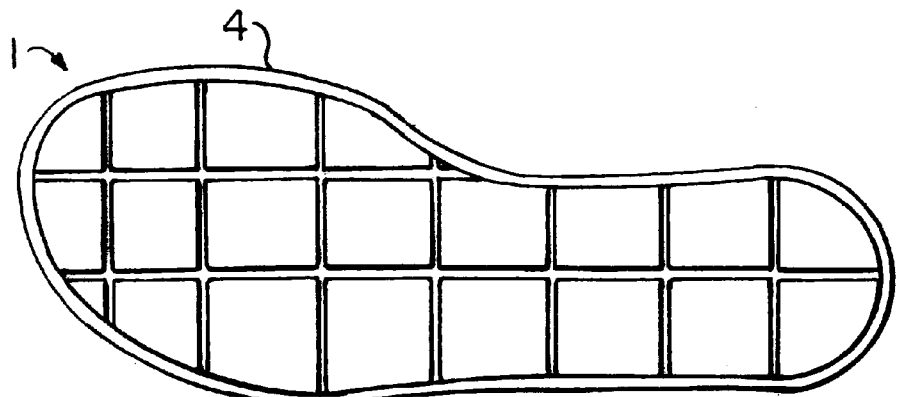
FIG. 4 is a top plan view of a pre-configured rigid sole used in the shoe of FIGS. 1–3.
Figure 5:
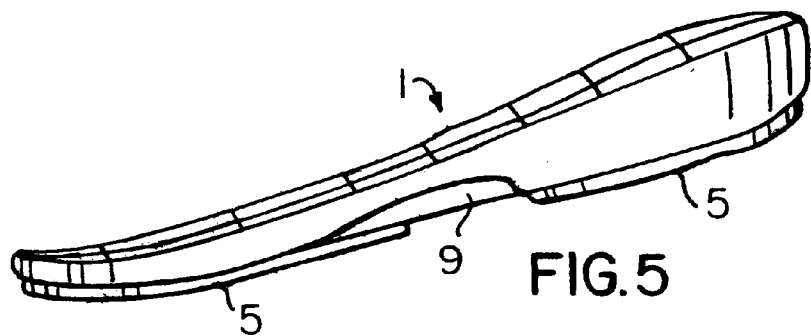
FIG. 5 is a side elevational view of the pre-configured rigid sole shown in FIG. 4.

The pre-configured rigid sole 9 may be molded from a material such as polyurethane or polystyrene, in the shape generally illustrated in FIGS. 4 & 5 of the drawings. There, it will be seen that the pre-configured rigid sole has an outline generally to the shape and size of the shoe being manufactured, with a non-deformable and rigid cross-sectional configuration, as shown in FIG. 5. When the pre-configured rigid shoe sole 9 is attached to the rubber outsole 5 and the padded upper insole 13, the rigid sole 9 will cause the outsole 5 and the padded upper insole 13 to conform to the pre-configured rigid shape, particularly insofar as the cross-sectional configuration of the rigid sole 9 is concerned . Thus, a user's foot, when resting upon the shoe insole will be maintained in a stable, secure and nonmoving position by the pre-configured rigid sole 9, while the padded upper insole 13 provides comfort and cushioning to the user's foot.

The padded upper insole 13 may be made from any suitable cushioning materials such as foam rubber or the like. The outer lining 11 covering the pre-configured rigid insole or platform 9, like the outer lining of the remainder of the shoe 1, is preferably formed from a porous synthetic polyamide material, such as "Nylon" or the like, provides a clean and smooth exterior surface, while allowing breathing for air movement therethrough, which is particularly useful in connection with the other components of the shoe 1, as will become apparent. The inner lining 15 covering the padded upper insole 13 is preferably formed from a terry cloth lining material so that it will provide a comfortable surface soft to the foot skin of a user, while absorbing any sweat or moisture from the user's foot. The terry cloth inner lining 15 also permits easy washing of those portions of the shoe which come into contact with the user's foot. The aforesaid pre-configured rigid insole 3 is also constructed to enable an arch support or the like to be placed thereon, as may be needed.

Figure 9:
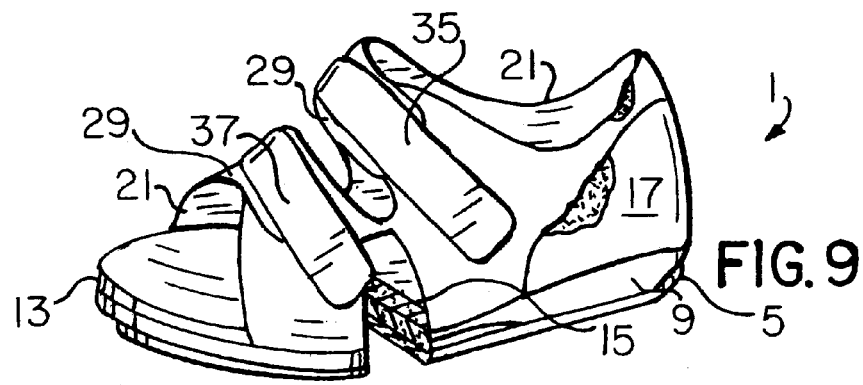
FIG. 9 is a fragmentary perspective view of a the post operative shoe shown in FIGS. 1–8 with several cut-out sectional views.
Figure 10:
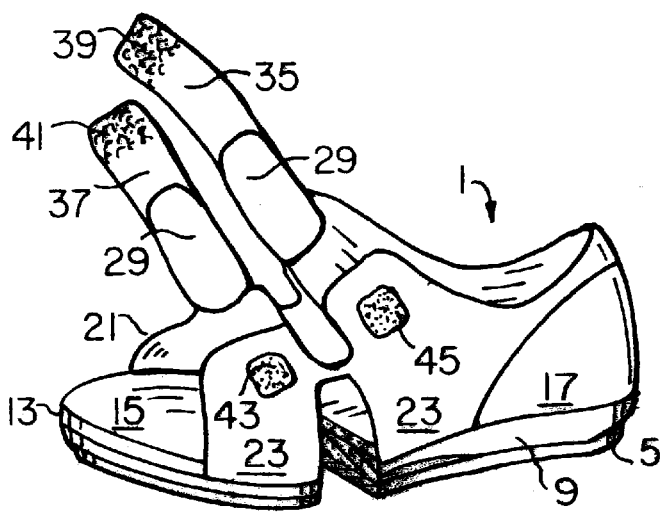
FIG. 10 is a framentary perspective view of a portion of the shoe illustrated in FIG. 9 of the drawings.
Figure 11:
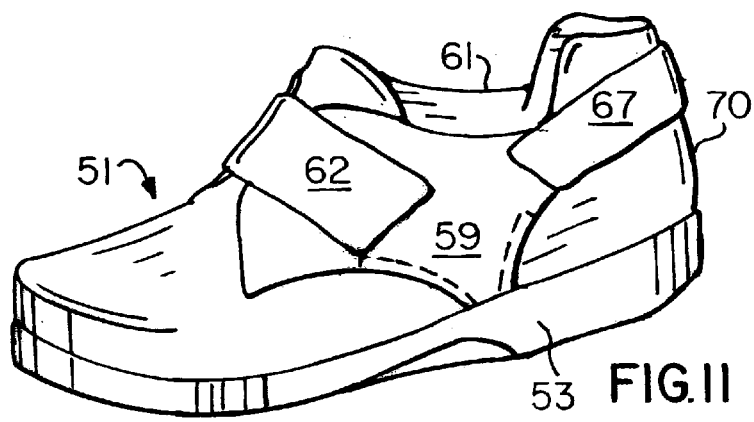
FIG. 11 is a perspective view of a second shoe used on the left foot and in the closed position in the post operative shoe system of the present invention.
Figure 12:
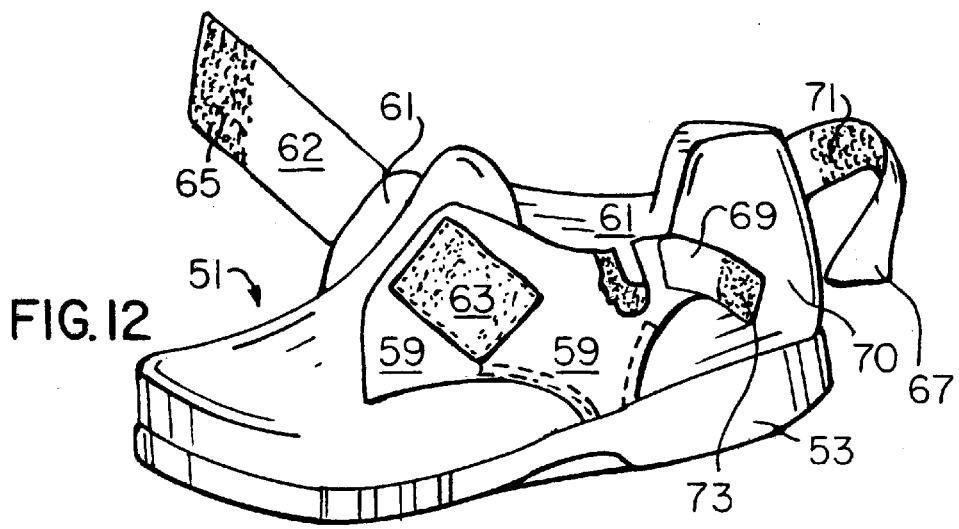
FIG. 12 is a perspective view of the shoe construction shown in FIG. 11 of the drawings in an open condition, prior to the insertion of a user's foot therein.
Figure 13:
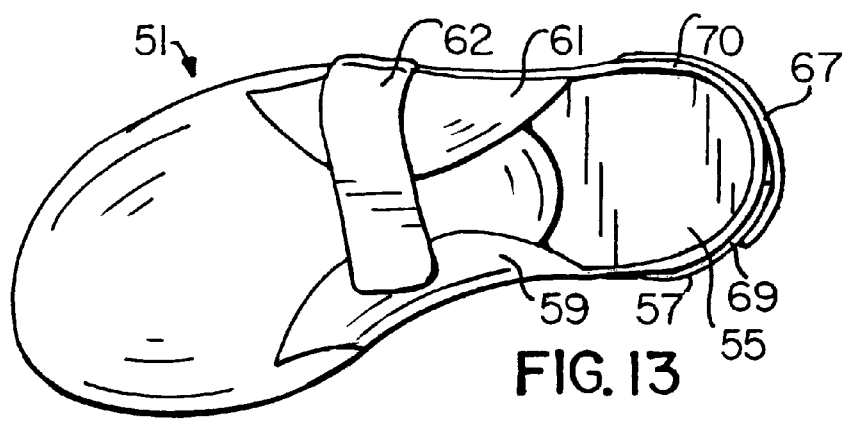
FIG. 13 is a top plan view of the right shoe illustrated in FIG. 14, showing the shoe in a fully closed position.
Figure 14:
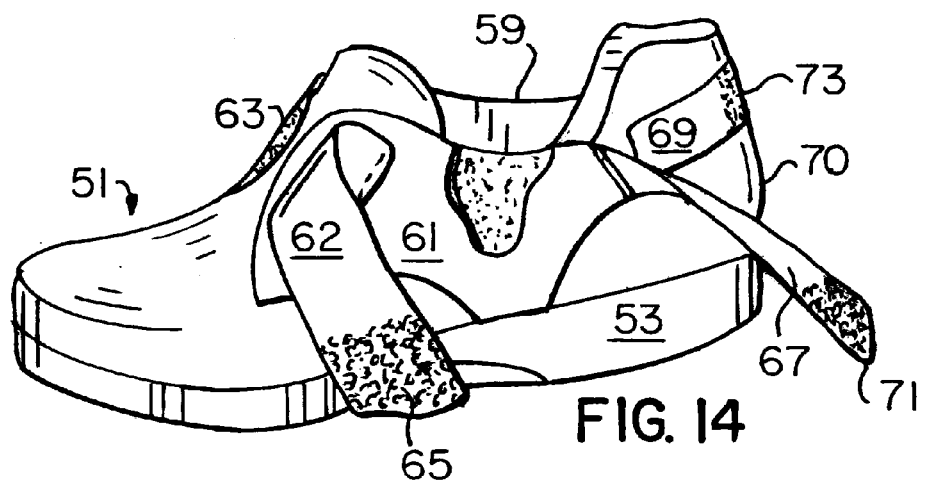
FIG. 14 is a side elevational view of the shoe illustrated in FIG. 13 of the drawings.

Attached to the rear of the shoe sole 9 is a counter 17 configured and shaped as a shoe heel. The counter 17 is supported by a molded and rigid thermo-counter 19, both of such elements being attached to the rigid insole 9 and the padded upper insole 13 of the pre-configured rigid shoe sole 9 as best seen in FIG. 9 of the drawings. As will be appreciated, the counter 17, including the rigid thermo-counter 19, provides a secure and stable support to the heel of the user. The outer lining 11 also covers the counter 17.

An inner and outer vamp 21, 23 are assembled to the shoe sole 9 and the counter 17 on opposite sides of each shoe 1 and include a toe cut-out section, shown with a phantom reference line 24 at the front end of each shoe 1, as shown in 1–10 of the drawings. The manner in which the inner and outer vamps 21 and 23 are attached to the shoe sole 9 and the counter 17 are again best illustrated in FIGS. 9–10 of the drawings. The inner and outer vamps 21 and 23 include end extensions not shown which are assembled or attached by sewing to the counter 17 in a typical manner, in order to attach the inner and outer vamps 21 and 23 to the counter 17.

Because the foot shape of different user's will vary along inner and outer areas thereof, the inner and outer vamps 21 & 23 are shaped to conform to a typical user's foot, as will be appreciated. This is best illustrated in FIG. 6 of the drawings where the inner and outer vamps 21 and 23 are shown in an open position prior to the insertion of a user's foot into the shoe 1.

In order to allow a user's foot to be fastened or secured to each shoe 1, the present invention employs a unique double closure fastener system employing releasably adjustable complementary interfitting releasable fastener elements. Specifically, it will be noted that a tongue element 29 is part of one side of the inner vamp 21, again best illustrated in FIG. 6 and in FIG. 15 of the drawings. Like other elements of the shoe, the outer lining of the tongue 29 is preferably formed from the porous "Nylon" type material; while the inner surface contacting the user's foot utilizes the terry cloth material. Along the outer surface 21a of the tongue 29, a strip of "Velcro" material 31 or the like is positioned and arranged to cooperate with a complementary "Velcro" strip 33 on the inner surface of inside surface of the outer vamp 23, in order to provide a releasably adjustable interfitting attachment of the inner and outer vamps 21 and 23 including the tongue 29 relative to the size and shape of a user's foot, as will be appreciated. The complementary interfitting fastening elements, such as the "Velcro"-type fasteners, employ a multiplicity of hooks on one or the other of the strips 31 and 33, while the other employs a multiplicity of loops, to permit the releasable adjustable fastening interengagement, as is typical with "Velcro" type fasteners.

Figure 7:
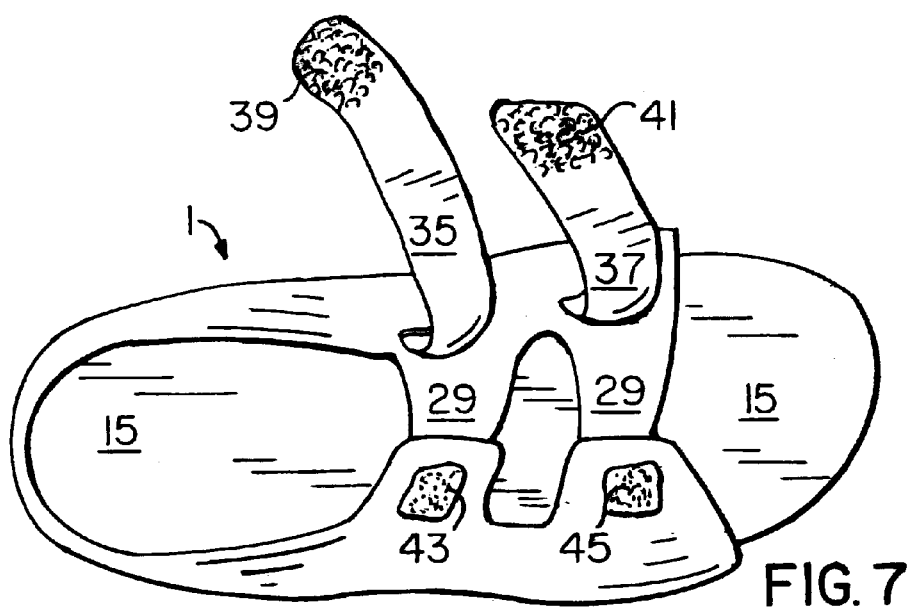
FIG. 7 is a top plan view of the shoe illustrated in FIGS. 1–3 and 6 of the drawings illustrating partial closing of the shoe.

Although the complementary interfitting fastener element strips 31 and 33 provided on the tongue 29 and outer vamp 23, respectively, will facilitate the attachment or mounting of the shoe 1 to a user's foot, the present invention, as shown in FIG. 7, further employs a pair of strap elements 35, 37 attached to the outer surface of the inner vamp 21 and having "Velcro"-type fastening strips 39 and 41 respectively on the strap elements 35, 37 for complementary interfitting fastening engagement with velcro-type strips 43 and 45 provided on the outer surface 23a of the outer vamp 23.

Figure 3:
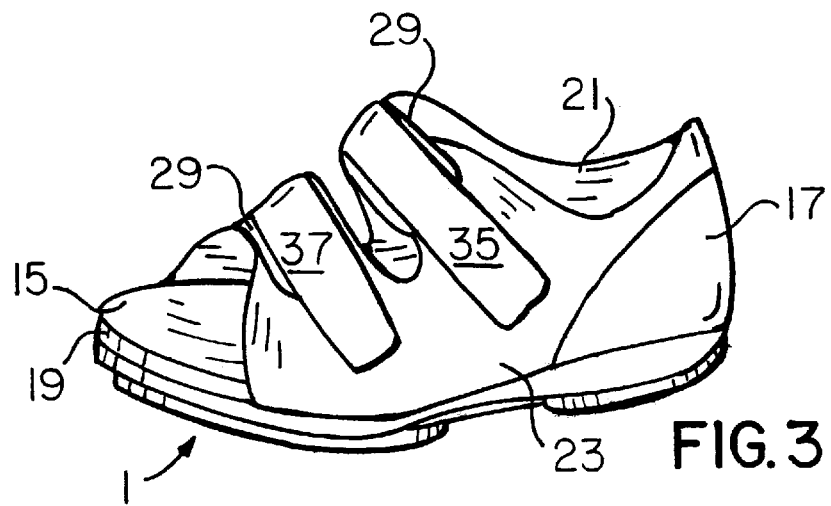
FIG. 3 is a left side elevational view of the shoe illustrated in FIG. 1.
Figure 6:
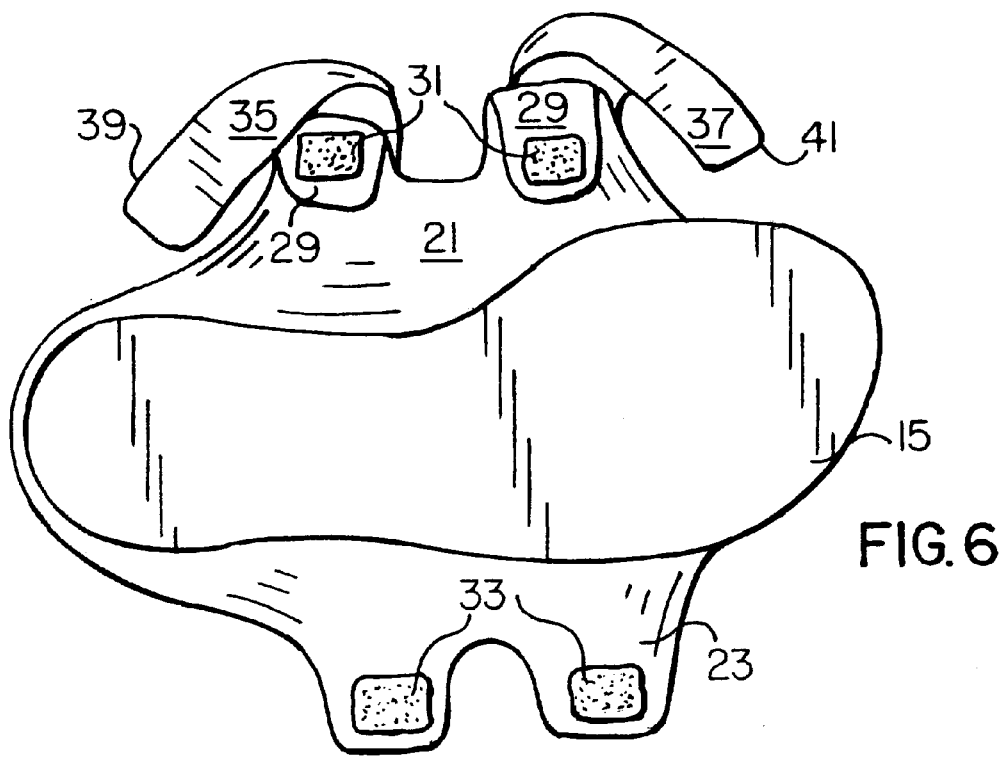
FIG. 6 is a top plan view of the post operative shoe shown in FIGS. 1–3 of the drawings in an open position just prior to the insertion of a user's foot into the shoe.
Figure 8:
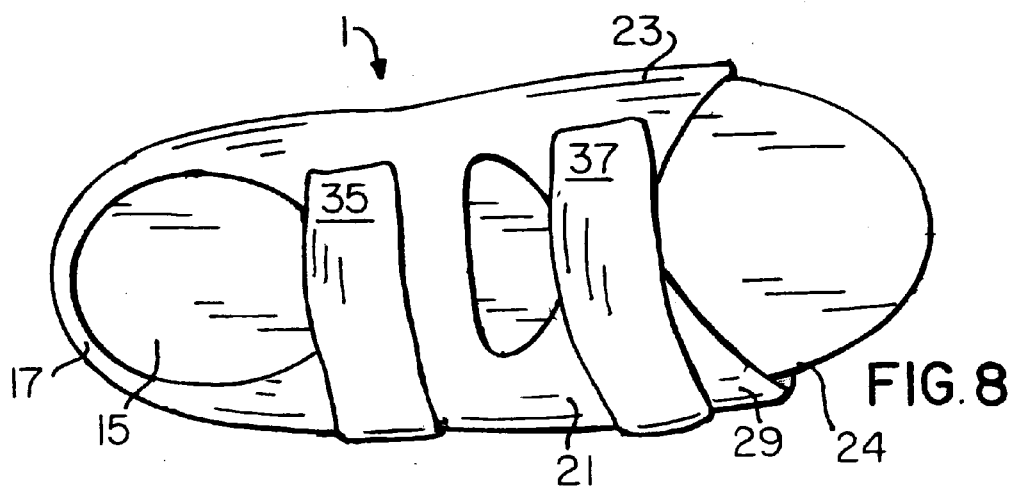
FIG. 8 is a top plan view of the same shoe illustrated in FIG. 1.
Figure 15:
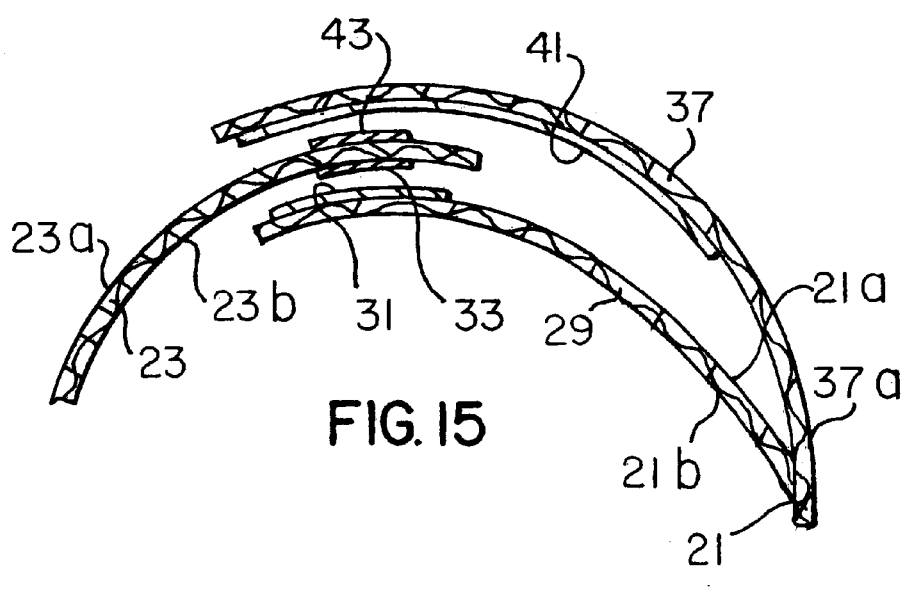
FIG. 15 is a section view, slightly exploded, of the post operative shoe of FIG. 1, showing especially the two vamps, tongue and strap in their overlappig and attached orientation.

By referring to the assembled shoe shown in various positions in FIGS. 1–3 of the drawings, together with the fully opened and partially closed shoe illustrations of FIGS. 6–7, with the fully closed top view illustration of the shoe in FIG. 8 of the drawings, it will be seen how the unique double closure fastening system of the present invention is employed. With the shoe fully opened, as shown in FIG. 6 of the drawings, a user's foot is placed upon the outer terry cloth lining 15 of the shoe insole 13. Then the inner and outer vamps 21 and 23 are brought over the top of the user's foot with the fastener strip 31 on the tongue 29 being brought into releasably adjustable fastening engagement relative to the fastener strip 33 on the inside surface of the outer vamp 23. Thereafter, the strap elements 35 and 37 with associated fastening strips 39 and 41, respectively, are drawn across the user's foot and into fastening engagement with the complementary fastening strips 43 and 45 mounted on the outer surface of the outer vamp 23, as best seen in FIGS. 7–8 and 15 of the drawings. The unique double closure fastening system, employing the "Velcro"-type fastening strips, not only enables releasably adjustable fastening engagement, but securely attaches the shoe 1 in place on the user's foot, thus eliminating any slippage at the heel or even the sensation that the shoe may be coming off.

During the first 6–8 weeks following surgery, each shoe 1 can thus be used to securely hold the foot of a surgical patient in a rigid and secure position, while affording comfort to the user when the shoe 1 is in place, as well as ease of use and convenience to the user in placing or removing the shoe 1 on the user's foot.

Following the initial convalescent period of 6–8 weeks, a second pair of shoes having the shoe construction shown in FIGS. 11–14 may be employed in the post operative shoe system of the present invention. The shoe 51, shown in FIGS. 11–14, is desirably used in the 3–4 month period following surgery. Each such shoe 51 includes a pre-configured rigid shoe sole including a molded rubber outsole or shoe base 53 molded to the shape illustrated in FIGS. 11–13, with a padded upper insole 55 attached to the outsole 53 including a terry cloth type outer lining 57.

Each shoe 51 further includes an inner and outer vamp 59, 61 respectively. The inner and outer vamps 59, 61 are assembled to the shoe sole intermediate to the outsole 53 and the padded upper insole 55, as illustrated. Across the top of the user's foot, the inner and outer vamps 59, 61 are releasably adjustably attached to one another through a strap 62 the "Velcro"-type complementary interfitting fastening elements 63, 65 provided on the inner vamp 59 and the strap 62, respectively. The inner and outer vamps 59 and 61 further include the heel strap elements 67, 69, with the strap 67 extending around the rear counter 70 and the heel of the user; and the strap 69 being much shorter than the strap 67, as illustrated in FIGS. 11–14. Adjacent the outer free ends of each of the strap elements 67, 69 are complementary "Velcro"-type interfitting fastener elements 71, 73 which are also adapted to be releasably adjustably attached to one another, as illustrated in the drawings. Thus, each shoe constructed like the shoe 51 illustrated in FIGS. 11–14 includes a releasably adjustable strap across the top of a user's foot, via the complementary interfitting fastener elements 63, 65 attached to the inner and outer vamps 59 and 61, respectively, while the strap elements 67, 69 attached to the inner and outer vamps 59 and 61, respectively, are also releasably adjustably attached around the heel of a user which is positioned inside of the rear counter 70, through the complementary interfitting fastening elements 71, 73. As in the shoe construction 1 illustrated in FIGS. 1–10 of the drawings, the shoe construction shown in FIGS. 11–14 of the drawings includes an inner lining 7, for the vamps and strap elements which is preferably made from a terry cloth type material while the outer lining for the shoe 51 has the vamps and strap elements made from a porous synthetic polyamide material such as "Nylon". This provides a clean, sanitary exterior for the shoe 51 while allowing air to enter into the shoe through the outer lining 7. The inner lining 7 also absorbs sweat or other moisture from a user's foot, but can be readily washed, as may be needed.

From the foregoing, it will now be appreciated that the post operative shoe system of the present invention, including a first pair of shoes constructed like the shoe 1 in FIGS. 1–10 and 15 of the drawings and a second pair of shoes constructed like the shoe 51 in FIGS. 11–14 of the drawings facilitates recovery of the foot surgical patient, both immediately following surgery, as well as after an initial convalescent period.

In view of the above, it will be seen that the several objects and features of this invention are achieved and other advantageous results obtained.

As various changes could be made in the above constructions without departing from the scope of the invention, it is intended that all matter contained in the above description or shown in the accompanying drawings shall be interpreted as illustrative and not in a limiting sense.

What is claimed is:

1. A post operative shoe for facilitating the recovery of a foot and for comfortably encompassing that foot while not in a cast, said shoe comprising:
   a pre-configured sole;
   a pair of vamps assembled to opposite sides of said sole and defining an inner vamp and an outer vamp;
   said vamps in combination having sufficient size to overlap each other over the top of an encompassed foot;

both said vamps having upper surfaces and lower surfaces;

a fastener system;

said fastener system having first means for releasably and adjustably attaching said lower surface of said outer vamp over and against said upper surface of said inner vamp;

said fastener system having a second means, independent of said first means, for releasably being attached over both said upper surfaces of said vamps to additionally inhibit said vamps from becoming unattached from each other.

2. A post operative shoe according to claim 1 in which, said fastener system second means includes;

strap means having one end secured to said upper surface of said inner vamp; and said strap means having sufficient length to overlie said upper surfaces of both said vamps, when said outer vamp is attached over said inner vamp by said first means of said fastener system.

3. A post operative shoe according to claim 2 in which said fastener system further includes;

a tongue extending from said inner vamp toward said outer vamp; and both said strap means and said tongue having free ends, between which said outer vamp becomes positioned and is adjustably attached.

4. A post operative shoe according to claim 2 in which, at least said strap means and one of said vamps includes releasable fastener elements.

5. A post operative shoe according to claim 2 in which, said strap means comprises a pair of strap elements spaced apart and secured to said inner vamp.

6. A post operative shoe according to claim 5 in which said fastener system further includes;

a pair of tongues extending from said inner vamp toward said outer vamp;

said tongues being spaced apart and aligned respectively below said spaced apart strap elements; and said strap elements and said tongues having free ends, between which said upper vamp becomes positioned and is adjustably attached.

7. A post operative shoe according to claim 1 in which, said vamp lower surfaces are made from soft and washable material which come in surface contact with the foot when said outer vamp is attached over said upper surface of said inner vamp.

8. A post operative shoe according to claim 1 further including, a counter constructed to include a heel;

said counter being assembled to said sole;

said counter having an inner surface which will come into contact with the heel of the foot; and said inner surface is of a soft material.

9. A post operative shoe according to claim 1 in which, said shoe has an outer surface of porous, synthetic polyamide.

10. A post operative shoe according to claim 1 and, in combination therewith, a second shoe for the same foot;

said second shoe to be worn after an initial convalescent period during which said post operative shoe can be worn;

said post operative shoe and said second shoe defining a post operative shoe system;

said second shoe having:

a pair of opposing vamps and a heel counter, each secured to a sole;

said heel counter also being attached to both said vamps, to form a continuous, uninterrupted peripheral covering around the heel of a foot;

strap means secured to at least one of said opposing vamps and oriented to overlie the periphery of said heel counter; and sand strap means having a free end including adjustable attaching means for regulating the distance around the periphery of said heel counter to adjustably tighten said second shoe around the heel of the foot.

11. A post operative shoe to be worn during an initial portion of convalescence, to protect a foot which is not in a cast;

said post operative shoe comprising a sole and a pair of vamps respectively secured to opposite sides of said sole;

said vamps each having an upper surface and a lower surface;

a fastener system means secured to one of said vamps at one location thereof and having a first part and a second part;

said first part adjustably attachable to said lower surface of the other of said vamps and being in the form of a tongue which is oriented to have a free end extending to underlie said lower surface of said other vamp; and said second part adjustably attachable to said upper surface of the other of said vamps and being in the form of a strap which passes over said tongue and having a free end which becomes positioned over said upper surface of said other vamp.

12. A post operative shoe according to claim 11; and a second shoe in combination with said post operative shoe to define a shoe system, said second shoe also being for that foot, to be worn during a second period of convalescence, subsequent to a first period of convalescence when said cost operative shoe is worn, said second shoe comprising:

a pair of vamps respectively secured to the opposite sides of a rigid sole;

a heel counter secured to said sole and said vamps and defining a continuous covering having a peripheral length around the heel of that foot; and tightening means associated with said heel counter for regulating its said peripheral length to tighten said heel counter around the heel of that foot.

13. A post operative shoe according to claim 12 in which said tightening means comprises:

strap means secured to at least one of said vamps and oriented to pass around said heel counter;

said strap means including fastening means for adjustably fastening said strap means to at least one of said heel counter and the other of said vamps.

14. A post operative shoe according to claim 11 in which;

at least said strap and said tongue have, proximate to their said free ends, attachment means, for attachment to said other vamp.

15. A post operative shoe according to claim 14 in which; said attachment means comprises "hook and loop" type fasteners.

16. A post operative shoe according claim 14 in which; said attachment means consists of "hook and loop" material for adjustably mating with "hook and loop" material on said opposite surfaces of said other vamp.

* * * * *